United States Patent
Kirenko et al.

(10) Patent No.: US 10,509,967 B2
(45) Date of Patent: Dec. 17, 2019

(54) OCCUPANCY DETECTION

(71) Applicant: KONINKLIJKE PHILIPS N.V., Eindhoven (NL)

(72) Inventors: Ihor Olehovych Kirenko, Veldhoven (NL); Mukul Julius Rocque, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/748,730

(22) PCT Filed: Aug. 10, 2016

(86) PCT No.: PCT/EP2016/068997
§ 371 (c)(1),
(2) Date: Jan. 30, 2018

(87) PCT Pub. No.: WO2017/025546
PCT Pub. Date: Feb. 16, 2017

(65) Prior Publication Data
US 2019/0012546 A1   Jan. 10, 2019

(30) Foreign Application Priority Data
Aug. 10, 2015   (EP) .................................... 15180330

(51) Int. Cl.
*G06K 9/00* (2006.01)
*G06T 7/246* (2017.01)
(Continued)

(52) U.S. Cl.
CPC ........ *G06K 9/00771* (2013.01); *A61B 5/1115* (2013.01); *A61B 5/1128* (2013.01);
(Continued)

(58) Field of Classification Search
CPC ... A47C 7/62; E05Y 2900/608; Y10S 901/01; Y10S 901/47; A47B 97/00; E05F 15/73;
(Continued)

(56) References Cited

U.S. PATENT DOCUMENTS

| 6,049,281 A | 4/2000 | Osterweil |
| 7,714,728 B2 | 5/2010 | Koblasz |

(Continued)

FOREIGN PATENT DOCUMENTS

| JP | 2008092538 | | 4/2008 |
| JP | 2011-86286 A | * | 4/2011 |

OTHER PUBLICATIONS

Schulze, et al., "Concept and Design of a Video Monitoring System for Activity Recognition and Fall Detection", LNCS 5597, pp. 182-189, 2009.

(Continued)

*Primary Examiner* — Hung Q Dang

(57) ABSTRACT

An apparatus for detecting when a subject has exited an item of furniture is provided. The apparatus comprises a camera adapted to be arranged, when in use, below the underside of an item of furniture having an upper side for supporting a subject, the underside being opposite to the upper side, and a processing unit. The camera captures sequential images that do not include the upper side of the item of furniture, the images having a foreground corresponding to a region below the underside of the item of furniture and a background corresponding to a region adjacent the item. The processing unit receives images from the camera; detects, for each image, an edge corresponding to an edge of the item; detects the appearance of a feature contiguous with the edge; monitors how a detected feature changes over a time period; determines whether a change to the detected feature satisfies (Continued)

at least one predefined criterion for a subject exit event; and outputs a signal based on the determining.

20 Claims, 5 Drawing Sheets

(51) Int. Cl.
G06T 7/13 (2017.01)
G06T 7/73 (2017.01)
A61B 5/11 (2006.01)
A61B 5/00 (2006.01)

(52) U.S. Cl.
CPC ........ A61B 5/6891 (2013.01); G06K 9/00342 (2013.01); G06T 7/13 (2017.01); G06T 7/248 (2017.01); G06T 7/74 (2017.01); *G06T 2207/30196* (2013.01); *G06T 2207/30232* (2013.01)

(58) Field of Classification Search
CPC ................ E05F 15/43; E05F 2015/767; E05F 2015/434; G06T 2207/30204; G06T 15/10; G06T 7/60; G06T 19/006; G06T 2207/10016; B26D 5/007; G05D 1/0234; G05D 2201/0203; G05D 1/0274; G05D 1/024; G05D 2201/0215; G05D 1/0272; H01R 13/7039; G06Q 30/0621; A43B 1/0081; A43B 3/122
See application file for complete search history.

(56) References Cited

U.S. PATENT DOCUMENTS

| 7,987,069 | B2 | 7/2011 | Rodgers | |
|---|---|---|---|---|
| 10,074,184 | B2* | 9/2018 | Rocque | A61B 5/1115 |
| 2007/0136102 | A1 | 6/2007 | Rodgers | |
| 2009/0278934 | A1 | 11/2009 | Ecker | |
| 2012/0075464 | A1 | 3/2012 | Derenne | |
| 2012/0212582 | A1 | 8/2012 | Deutsch | |
| 2012/0229634 | A1 | 9/2012 | Laett | |
| 2013/0215248 | A1* | 8/2013 | Ishii | A61B 5/1113 348/77 |
| 2014/0092247 | A1* | 4/2014 | Clark | H04N 7/181 348/143 |
| 2014/0240479 | A1 | 8/2014 | Yasukawa | |
| 2014/0267663 | A1* | 9/2014 | Yasukawa | H04N 7/18 348/77 |
| 2015/0112151 | A1* | 4/2015 | Muhsin | A61B 5/002 600/301 |
| 2017/0046577 | A1* | 2/2017 | Rocque | A61B 5/6891 |

OTHER PUBLICATIONS

Capezuti, et al., "Bed-exit alarm effectiveness", Archives of Gerontology and Geriatrics, 2008.
Martinez, et al., "Automated Multi-Camera System for Long Term Behavioral Monitoring in Intensive Care Units", MVA, 97-100,2013.
Banerjee, et al., "Monitoring Patients in Hospital Beds Using Unobtrusive Depth Sensors", 2014 IEEE.

* cited by examiner

OCCUPANCY DETECTION

CROSS REFERENCE TO RELATED APPLICATIONS

This application is the U.S. National Phase application under 35 U.S.C. § 371 of International Application No. PCT/EP2016/068997, filed Aug. 10, 2016, published as WO 2017/025546 on Feb. 16, 2017, which claims the benefit of European Patent Application Number 15180330.1 filed Aug. 10, 2015. These applications are hereby incorporated by reference herein.

TECHNICAL FIELD OF THE INVENTION

The invention relates to an apparatus, system and method for detecting when a subject has exited an item of furniture.

BACKGROUND TO THE INVENTION

Detecting the movement and/or position of a subject is important in several healthcare applications. For example, it is often desired to prevent patients in hospital beds from moving in certain ways. As a result of medications, impaired memory, old age and/or other disabilities, patients who attempt to leave their beds without assistance often fall and injure themselves. Unassisted movement of a patient can also lead to medical devices attached to that patient becoming dislodged and ceasing to function properly.

However; the monitoring of patients who should not get out of bed without clinical assistance can place a significant burden on hospital staff.

Many current methods used for bed occupancy detection utilize a camera directed at the bed. In some examples a person (e.g. a medical professional) must constantly monitor the image feed from the camera. In other examples, such as the system described in US 2009/0278934, automated image analysis is used to detect bed exit events, but this requires complicated algorithms for detecting bed boundaries and classifying movements of the subject. Such algorithms can be confused by movements other than that of the subject (e.g. a blanket falling off the bed), leading to false alarms being raised when the subject is not attempting to exit the bed. Many such algorithms also require significant computational resource, since they continually estimate the position and/or motion of a monitored subject. Also, automated camera-based systems require recalibrating each time the relative position of the camera and the bed changes, and become unreliable if such recalibrations are not performed. An additional issue is the privacy of the monitored subject. It can be difficult to ensure that privacy is maintained when a monitoring system requires an image of the subject to be continually recorded.

Document US 2014/240479 A1 relates to an information processing apparatus that comprises a camera to capture images of a watching target person whose behavior is watched and of a bed that is used as a target object serving as reference for the behavior of the watching target person. From the acquired images, the apparatus detects a moving object area and presumes a given behavior of the watching target person based on the positional relationship between the moving object area and the target object.

There is therefore a need for an automated monitoring system which is reliable, unobtrusive and computationally efficient, and which is able to monitor subjects occupying hospital beds and/or other items of furniture to detect when a subject attempts to leave a bed or other item of furniture.

SUMMARY OF THE INVENTION

According to a first aspect of the invention, there is provided an apparatus for detecting when a subject has exited an item of furniture. The apparatus comprises a camera adapted to be arranged, when in use, beneath or below the underside of an item of furniture. The item of furniture has an upper side for supporting a subject, and the underside is opposite to the upper side. The camera is arranged to capture sequential images that do not include the upper side of the item of furniture, the images having a foreground corresponding to a region beneath or below the underside of the item of furniture and a background corresponding to a region adjacent the item of furniture. The apparatus further comprises a processing unit. The processing unit is arranged to receive the images from the camera; detect, for each received image, an edge corresponding to an edge of the item of furniture; detect, in the received images, the appearance of a feature contiguous with the edge; monitor how a detected feature changes over a time period; determine whether a change to the detected feature over the time period satisfies at least one predefined criterion for a subject exit event; and output a signal based on the determining.

In some embodiments the camera is arranged to capture sequential images including at least part of the underside of the item of furniture. In some such embodiments the edge corresponding to an edge of the item of furniture comprises an edge of the at least part of the underside of the item of furniture, such that a first portion of each image adjacent a first side of the edge shows the underside of the item of furniture and a second portion of each image adjacent a second, opposite side of the edge does not show the underside of the item of furniture.

In some embodiments the processing unit is arranged to detect a predefined one of the edges of each received image to be an edge corresponding to an edge of the item of furniture. In some embodiments the processing unit is arranged to detect the appearance of a feature contiguous with the edge by comparing a first image acquired at a first time, to a second image acquired at a second, later, time; and if a feature contiguous with the edge is present in the second image but is not present in the first image, determining that a feature has appeared contiguous with the edge.

In some embodiments the processing unit is arranged to monitor changes to a detected feature over a time period by determining a first value for a property of the feature in a first image acquired at a first time determining a second value for the property of the feature in a second image acquired at a second, later, time; and comparing the second value to the first value. In some such embodiments the property of the feature is any one of: size of the feature, shape of the feature, location of the feature; extension of the feature perpendicular to the shadow edge; depth of the feature.

In some embodiments the processing unit is arranged to monitor changes to a detected feature over a time period by: determining a rate of change of the detected feature over the time period, based on the first value, the second value, the acquisition time of the first image, and the acquisition time of the second image. In some embodiments the processing unit is arranged to monitor changes to a detected feature over a time period by determining a direction of motion of the detected feature over the time period.

In some embodiments the at least one predefined criterion for a subject exit event comprises a condition relating to a direction of motion of a detected feature. In some embodiments the predefined criterion for a subject exit event is defined such that motion of a detected feature in a direction away from the edge during the time period will be determined by the processing unit to satisfy the predefined criterion and motion of a detected feature toward the edge will be determined by the processing unit not to satisfy the predefined criterion. In some embodiments the predefined criterion for a subject exit event is defined such that motion of a detected feature in a direction into the plane of the received images during the time period will be determined by the processing unit to satisfy the predefined criterion and motion of a detected feature out of the plane of the received images will be determined by the processing unit not to satisfy the predefined criterion.

In some embodiments the apparatus is additionally for detecting when a subject has entered an item of furniture. In some such embodiments the processing unit is further arranged to determine whether a change to the detected feature over the time period satisfies at least one predefined criterion for a subject entry event. In some embodiments the predefined criterion for a subject entry event is defined such that motion of a detected feature over the time period in a direction away from the shadow edge or into the plane of the received images will be determined by the processing unit not to satisfy the predefined criterion.

In some embodiments the camera comprises a depth camera. In some embodiments the camera comprises a wide-angle camera.

There is also provided, according to a second aspect of the invention, a system for detecting when a subject has exited an item of furniture. The system comprises an item of furniture having an upper side for supporting a subject and an underside opposite to the upper side. The system further comprises a camera adapted to be arranged, when in use, beneath or below the underside of the item of furniture. The camera is arranged to capture sequential images that do not include the upper side of the item of furniture, the images having a foreground corresponding to a region beneath or below the underside of the item of furniture and a background corresponding to a region adjacent the item of furniture. The system further comprises a processing unit. The processing unit is arranged to receive the images from the camera; detect, for each received image, an edge corresponding to an edge of the item of furniture; detect, in the received images, the appearance of a feature contiguous with the edge; monitor how a detected feature changes over a time period; determine whether a change to the detected feature over the time period satisfies at least one predefined criterion for a subject exit event; and output a signal based on the determining.

There is also provided, according to a third aspect of the invention, a method for detecting when a subject has exited an item of furniture, wherein the item of furniture has an upper side for supporting a subject, and the underside is opposite to the upper side. The method comprises:

receiving sequential images captured by a camera arranged beneath or below the underside of the item of furniture, the images not including the upper side of the item of furniture and having a foreground corresponding to a region beneath or below the underside of an item of furniture and a background corresponding to a region adjacent the item of furniture;

detecting, for each received image, an edge corresponding to an edge of the item of furniture;

detecting, in the received images, the appearance of a feature contiguous with the edge;

monitoring how a detected feature changes over a time period;

determining whether a change to the detected feature over the time period satisfies at least one predefined criterion for a subject exit event; and outputting a signal based on the determining.

Thus, embodiments of the invention advantageously provide a system which can reliably and unobtrusively monitor movements of a subject occupying an item of furniture, whilst using considerably less computational resource than conventional camera-based monitoring systems. In this manner bed (or other furniture) exit events can be detected automatically, which can considerably reduce the monitoring burden on medical staff.

In the context of the present invention the camera being beneath or below the underside of an item of furniture preferably refers to the fact that the camera is, at least partially, in the projection (preferably the orthogonal projection) of the underside of the item of furniture on the floor, or on the ground, or on a surface on which the item of furniture rests, or on a surface on which the subject needs to walk on to get to, or away from, the item of furniture.

Also in the context of the present invention, the foreground and the background in the images captured by the camera are preferably arranged so that the foreground is closer to the camera than the background along a direction perpendicular to the focal plane of the camera.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE PREFERRED EMBODIMENTS

Figure 1:
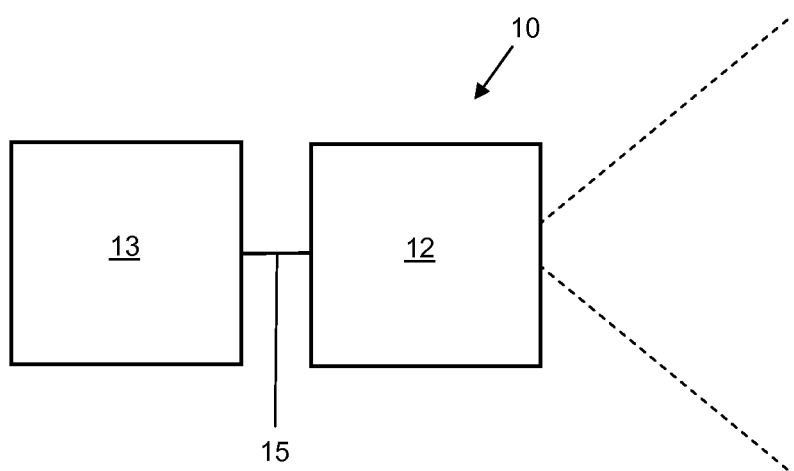
FIG. 1 is an illustration of an example apparatus for detecting when a subject has exited an item of furniture, according to a general embodiment of the invention.

FIG. 1 shows an apparatus 10 for detecting when a subject has exited an item of furniture, according to a general embodiment. The apparatus comprises a light a camera 12 and a processing unit 13.

The phrase "processing unit" is used herein to refer to an entity or system for processing, for example, those that process in response to a signal or data and/or those that process autonomously. A processing unit should be understood to encompass microprocessors, microcontrollers, programmable digital signal processors, integrated circuits, computer software, computer hardware, electrical circuits, application specific integrated circuits, programmable logic devices, programmable gate arrays, programmable array logic, personal computers, chips, and any other combination of discrete analog, digital, or programmable components, or other devices capable of providing processing functions.

The camera 12 is configured to be arranged, when in use, below the underside of an item of furniture, where the item of furniture has an upper side for supporting a subject and the underside is opposite to the upper side. The camera 12 is arranged to capture sequential images that do not include the upper side of the item of furniture, the images having a foreground corresponding to a region below the underside of the item of furniture and a background corresponding to a region adjacent the item of furniture. The field of view (FOV) of the camera 12 is shown by the dashed lines in FIG. 1. In some embodiments the camera 12 comprises a depth camera or sensor, e.g. a time of flight camera, a stereo camera, a range camera, a depth camera which uses structured IR light, etc. In some embodiments the camera 12 comprises a wide-angle camera, e.g. a camera which comprises a fish-eye lens. Advantageously, a camera which has a very wide FOV, such as that provided by a fish-eye lens, can often be arranged such that all edges of the underside of an item of furniture are within the FOV of the camera. This allows all sides of an item of furniture from which a subject could exit that item of furniture to be monitored using a single camera.

In some embodiments the apparatus 10 comprises multiple cameras. In some such embodiments each of the multiple cameras can be arranged to view a different background region adjacent an item of furniture. For example, in some embodiments a first camera can be arranged to view a background region adjacent a first side of an item of furniture and a second camera can be arranged to view a background region adjacent a second, opposite, side of the item of furniture. Advantageously this can enable all sides of the item of furniture from which it is possible for a subject to exit that item of furniture to be simultaneously monitored by the apparatus, without needing the subject-supporting surface of the item of furniture to be within any of the captured images. Privacy of a subject occupying the item of furniture can therefore be maintained. In some embodiments the multiple cameras comprise cameras of different types. In one example, the apparatus 10 comprises a 2D camera and a depth camera, which are arranged to view the same foreground and background regions. Advantageously, using a 2D camera and a depth camera in combination can make it easier to accurately segment features in the captured images.

The camera 12 is arranged to capture sequential images of the surface. In some embodiments the camera 12 is a 2-D camera. In some embodiments the camera 12 is a wide-angle camera. Preferably the FOV of the camera is wide enough to encompass a whole side of an item of furniture from which a subject may exit/enter that item of furniture. In some embodiments the camera 12 is a video camera, which is arranged to capture a video stream comprising a plurality of consecutive video frames. In some embodiments the camera is a still camera, arranged to capture a series of still images, e.g. during a recording period. In some embodiments the camera 12 is arranged to be attachable to the underside of an item of furniture, either directly or via a mounting member. In some such embodiments the camera 12 is arranged to be rigidly attachable to the underside of an item of furniture, such that it moves together with movements of the underside of the item of furniture. In some embodiments the camera 12 is arranged to be supported by a surface on which the item of furniture is resting, e.g. a floor.

In some embodiments the apparatus further comprises a light source (not shown), arranged to illuminate at least the background region adjacent the item of furniture. In some such embodiments the light source is a directional light source. In some embodiments the light source is a non-directional light source. In some embodiments the light source is comprised within the camera 12. In some embodiments the light source is arranged such that substantially all of the light emitted by the light source has a wavelength in a predefined range. In some embodiments the light source is arranged to emit light at a wavelength at which other light sources in the location where the apparatus is to be used do not emit a signification amount of light, or do not emit light at a high intensity relative to the intensity of light at that wavelength emitted by the light source. In some such embodiments the light source comprises an optical filter arranged to permit passage of light having a wavelength in the predefined range. In some embodiments the light source is arranged to emit near-infrared (IR) light. Advantageously, a light source which uses near-IR light can prevent visual disturbance to the subject or hospital staff.

In some embodiments in which the apparatus 10 comprises a light source arranged such that substantially all of the light emitted by the light source has a wavelength in a predefined range, the camera 12 is arranged to detect light of the same type as the light emitted by the light source. For example, in some embodiments in which the light source is arranged to emit near-IR light, the camera 12 is arranged to detect near-IR light and to generate images based on the detected near-IR light. In some embodiments in which the light source is arranged such that substantially all of the light emitted by the light source has a wavelength in a predefined range (e.g. by means of the light source comprising an optical filter), the camera is arranged to detect light having a wavelength in the predefined range. In some such embodiments the camera 12 comprises an optical filter arranged to permit the passage of light having a wavelength in the predefined range and to block the passage of light having a wavelength outside of the predefined range.

The processing unit 13 is arranged to receive the images from the camera 12, e.g. via a communications link 15. The communications link 15 may be wired or wireless. In some embodiments in which the apparatus comprises a 2D camera and a depth camera, the processing unit 13 is arranged to receive images from both the 2D camera and the depth camera. In some such embodiments the processing unit 13 is arranged to combine each image received from the 2D camera with a corresponding image, acquired at the same time, from the depth camera. In some embodiments the processing unit 13 is arranged to process the 2D images and the depth images in parallel.

In some embodiments in which the apparatus comprises a 2D camera and a depth camera/sensor, the processing unit 13 is arranged to receive images from both the 2D camera and the depth camera. In some such embodiments the apparatus is arranged to combine each image received from the 2D camera with a corresponding image, acquired at the same time, from the depth camera.

The processing unit 13 is further arranged to detect an edge corresponding to an edge of the item of furniture (i.e. an item of furniture which the camera 12 is arranged beneath) for each of the received images. In some embodiments (e.g. embodiments in which the camera is for arranging such that no part of the item of furniture is included in the images captured by the camera) the processing unit is arranged to detect an edge corresponding to an edge of the item of furniture by determining which edge of a received image is closest to an edge of the item of furniture (e.g. based on the orientation of objects or features included in the received image, and/or predefined rules stored in a memory of the processing unit 13), and selecting this closest edge to be the edge corresponding to an edge of the item of furniture. In some embodiments the processing unit 13 is arranged to detect a particular edge of a received image (e.g. a top edge) as defined with respect to the orientation of the camera 12, to be the edge corresponding to an edge of the item of furniture.

Figure 2A:
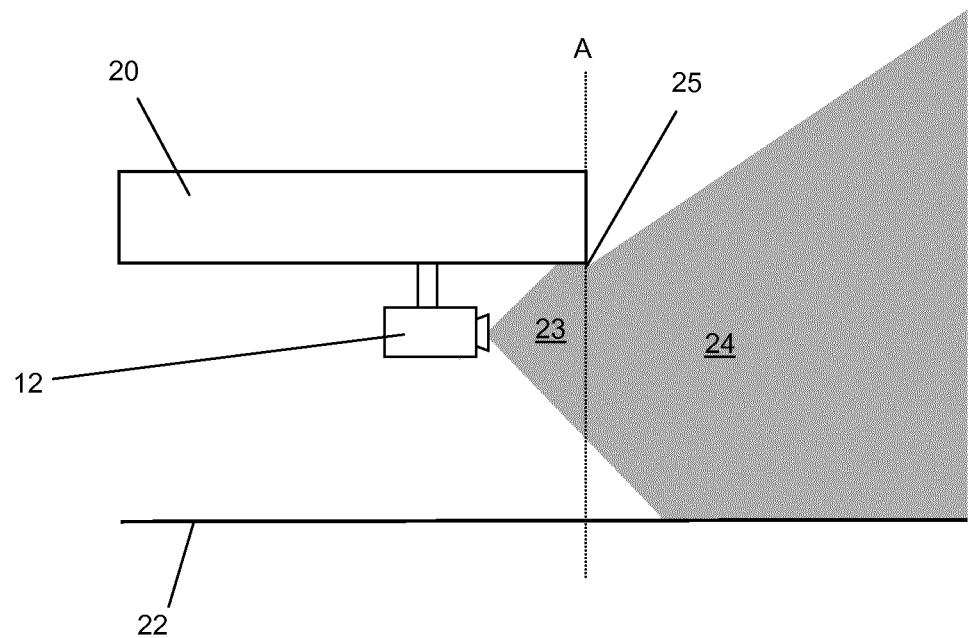
FIG. 2a shows a camera of the example apparatus of FIG. 1, in use in a first arrangement to capture images including a region adjacent a bed.

FIG. 2a shows a cross section through part of a bed 20 to which a camera 12 of an apparatus 10 is attached. The bed is resting on a floor 22. The FOV of the camera 12 is shown by the area shaded grey. It can therefore be seen that the images captured by the camera 12 will include, in the foreground, a region 23 which is below the underside of the bed 20, and, in the background, a region 24 which is adjacent the bed 20. The boundary between the foreground region 23 and the background region 24 is shown by the dotted line A. The camera 12 is a wide-angle camera and is located beneath, in particular below, the bed 20 such that an edge 25 of the underside of the bed 20 is within the FOV of the camera 12. Consequently the edge 25 will be included in the images acquired by the camera 12.

Figure 2B:
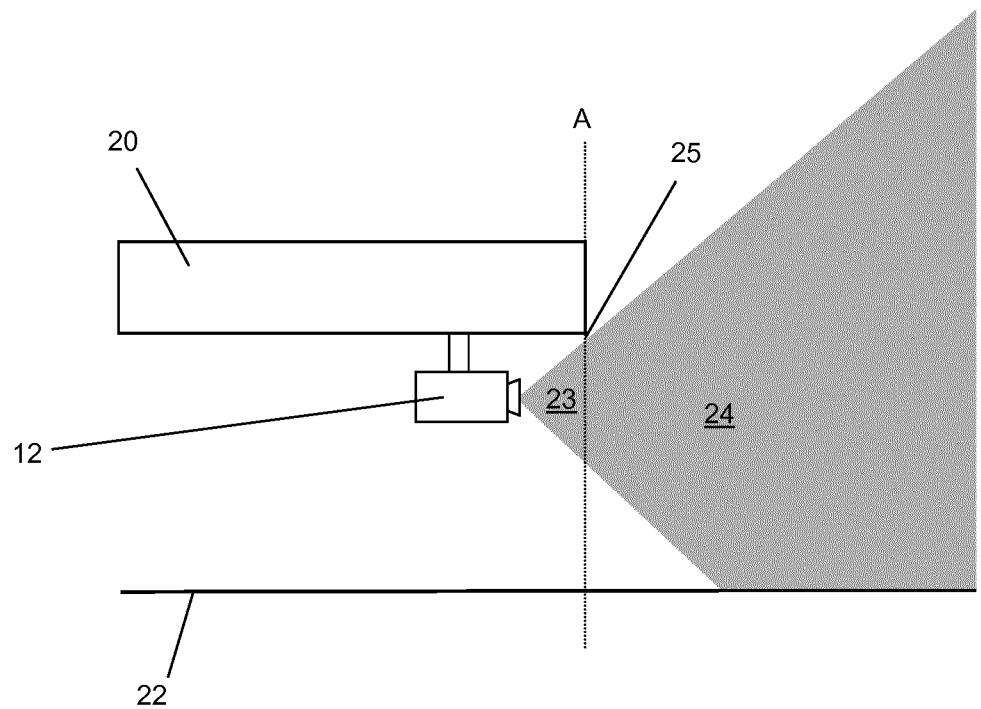
FIG. 2b shows a camera of the example apparatus of FIG. 1, in use in a second arrangement to capture images including a region adjacent a bed.

FIG. 2b shows an alternative arrangement of the apparatus 10 and the bed 20. In this example the camera 12 is located beneath the bed 20 such that the edge 25 of the underside of the bed 20 is not within the FOV of the camera 12. This has been achieved by reducing the distance between the camera 12 and the edge 25 of the underside of the bed. Consequently, with the arrangement of FIG. 2b, the edge 25 will not be included in the images acquired by the camera 12.

In embodiments (such as that shown in FIG. 2b) in which an edge of an item of furniture beneath which the camera 12 is arranged is not included in the received images, the processing unit is arranged to, for each received image, detect one of the edges of the image to be an edge corresponding to an edge of the item of furniture. Any suitable algorithms or techniques known in the art may be used to effect such a detection. Preferably the processing unit 13 is arranged to detect the edge of the image which is closest to an edge of the item of furniture to be an edge corresponding to an edge of the item of furniture (e.g. as can be seen from FIG. 2b, for a camera below an item of furniture, generally the top (i.e. furthest from the floor) of each received image will be closest to an edge of the item of furniture.

In embodiments (such as that shown in FIG. 2a) in which an edge of an item of furniture below which the camera 12 is arranged is included in the received images, the processing unit 13 may be arranged to use any suitable edge detection algorithm(s) known in the art to detect the edge of the item of furniture in the received images. In preferred embodiments, the light source (which need not form part of the apparatus 10, instead it could comprise a light source of a room in which the apparatus 10 is being used, e.g. a ceiling light, a lamp, or a window) is not located below the item of furniture being monitored. This means that the edge of the item of furniture will appear as a silhouette in the received images. A silhouette is generally a well-defined, high-contrast object, and is therefore straightforward to detect using simple image processing techniques. Consequently the computational resource required for detecting the edge of the item of furniture is low compared to what would be required, e.g., for detecting a subject on the bed. However, other embodiments are possible in which a light source is provided beneath (preferably below) an item of furniture being monitored. In particular, in embodiments in which the camera 12 comprises a depth camera, the depth camera may comprise or be associated with a dedicated light source. The edge of the item of furniture need not appear as a linear feature in the received images, even if it is linear in the physical world. For example, in embodiments where the camera comprises a fish-eye lens, a straight edge of an item of furniture will appear as a curved edge in the received images.

The processing unit 13 is further arranged to detect, in the received images, the appearance of a feature contiguous with a detected edge. A feature may comprise, for example, a local deformation of the edge, a shadow or silhouette touching or overlapping the edge, an object touching or overlapping the edge, etc. It will be appreciated that the nature of the feature can depend on the type of the camera 12 used to acquire the received images. For example, in embodiments in which the camera 12 comprises a depth camera, the feature can comprise a well-defined region of an image having a different depth to its surroundings. The nature of the feature can also depend on whether the edge is an edge of an image, or is an edge (i.e. of the item of furniture) which is included in a received image. For example, it will be appreciated that an edge of the image cannot deform, but that it is possible for an object, silhouette or shadow to appear which touches or overlaps the edge of an image.

In some embodiments, the processing unit is arranged to detect features which appear at a lower (i.e. closest to a surface on which the item of furniture is resting) side of an edge which is included in the received images and is not arranged to detect (or is arranged not to detect) features which appear at the opposite (upper) side of such an edge. Since the region of the image above a detected edge will show only the underside of the item of furniture, any features appearing in this region are expected to be artefacts and not indicative that a subject is exiting the item of furniture. Arranging the processing unit 13 such that it does not detect features which appear at the upper side of a detected edge can therefore improve the reliability of the apparatus 10.

In some embodiments the processing unit 13 is arranged to detect the appearance of a feature contiguous with a detected edge by comparing a first image (which may, in some embodiments, comprise a video frame) acquired at a first time, to a second image (which may, in some embodiments, comprise a video frame) acquired at a second, later, time. The second time may be immediately (as far as is possible with regards to how frequently the camera 12 is arranged to acquire images/video frames) after the first time, or alternatively may be a predetermined length of time after the first time. In some such embodiments, if a feature contiguous with the detected edge is present in the second image but is not present in the first image, the processing unit is arranged to determine that a feature has appeared contiguous with the edge. In some embodiments the processing unit 13 is arranged to perform such a comparison in respect of each consecutive (in time) pair of received images.

The processing unit 13 is further arranged to monitor how a detected feature (i.e. a feature which has appeared contiguous with a detected edge) changes over a time period. In some embodiments the processing unit is arranged to monitor changes to a detected feature over a time period by determining a first value for a property of the feature in a first image acquired at a first time; determining a second value for the property of the feature in a second image acquired at a second, later, time; and comparing the second value to the first value. The property of the feature can be, e.g., size of the feature, area of the feature, shape of the feature, location of the feature; extension of the feature perpendicular to the edge, objective depth of the feature in the image, depth of the feature relative to another part of the image, etc. In some embodiments the processing unit 13 is arranged to determine a rate of change of the detected feature over the time period, based on the first value, the second value, the acquisition time of the first image, and the acquisition time of the second image. In some embodiments the processing unit is arranged to monitor changes to a detected feature over a time period by determining a direction of motion of the detected feature over the time period. In embodiments in which the camera 12 comprises a depth camera, a direction of motion of a detected feature can be into or out of the plane of the image, as represented by an increase or decrease in the depth of the feature in successive images.

Figure 3A:
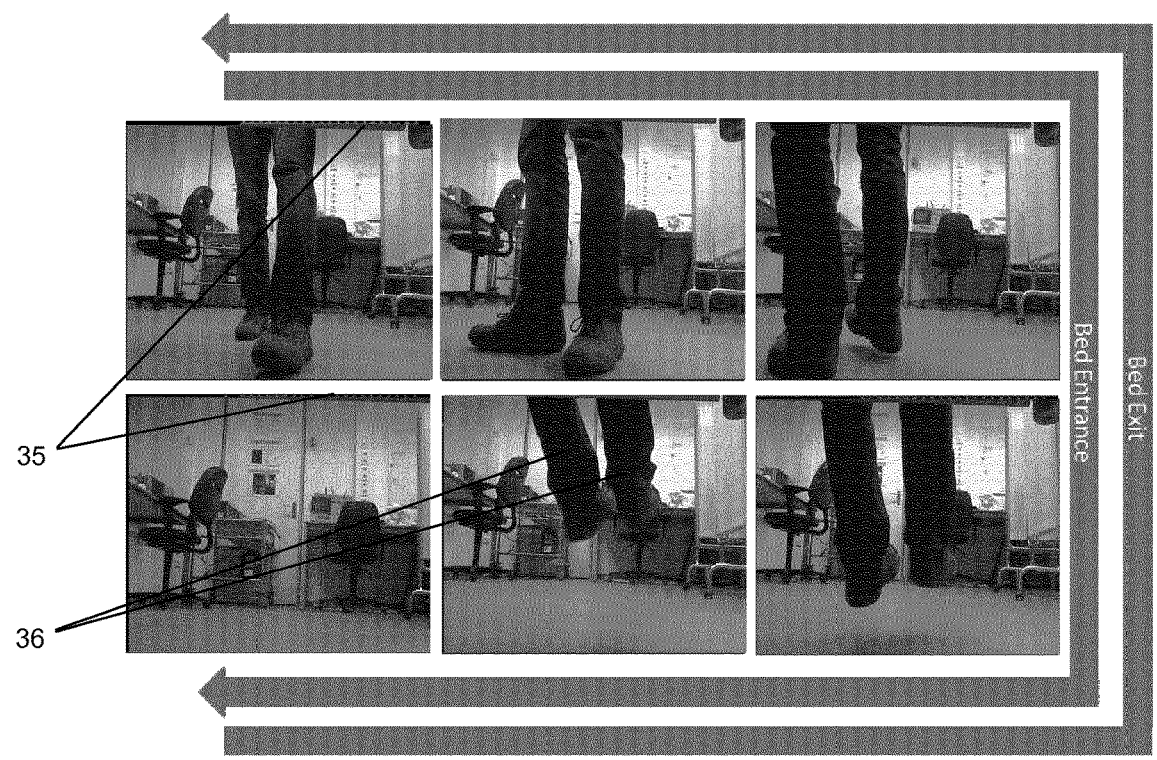
FIG. 3a shows an example series of 2D images representing a subject exit event, according to an embodiment of the invention.

FIG. 3*a* shows an example set of images obtained by a visible-light 2D camera, representing (if followed anti-clockwise from the bottom left image) a bed exit event (or, if followed clockwise from the top left image, a bed entry event). In the first (i.e. bottom left) image an edge 35 of the underside of a bed is visible as a black line spanning the top edge of the image. A background region adjacent the bed is also visible, below the edge 35. No features are present in this image which are contiguous with the edge 35. In the next (bottom middle) image a subject's legs have appeared as features 36. The legs are visible in the image as two high-contrast objects contiguous with the edge 35. In subsequent images the leg features 36 increase in size and in extension relative to the edge 35 (as the subject lowers them toward the floor. In an example embodiment of the apparatus 10, the processing unit is arranged to detect the edge 35 as an edge corresponding to an edge of an item of furniture, to detect the legs as features which have appeared contiguous with the detected edge, and to monitor changes to the detected leg features 36 by determining an extension of one or each leg feature in each successive image and comparing extension values between pairs of consecutive images.

Figure 3B:
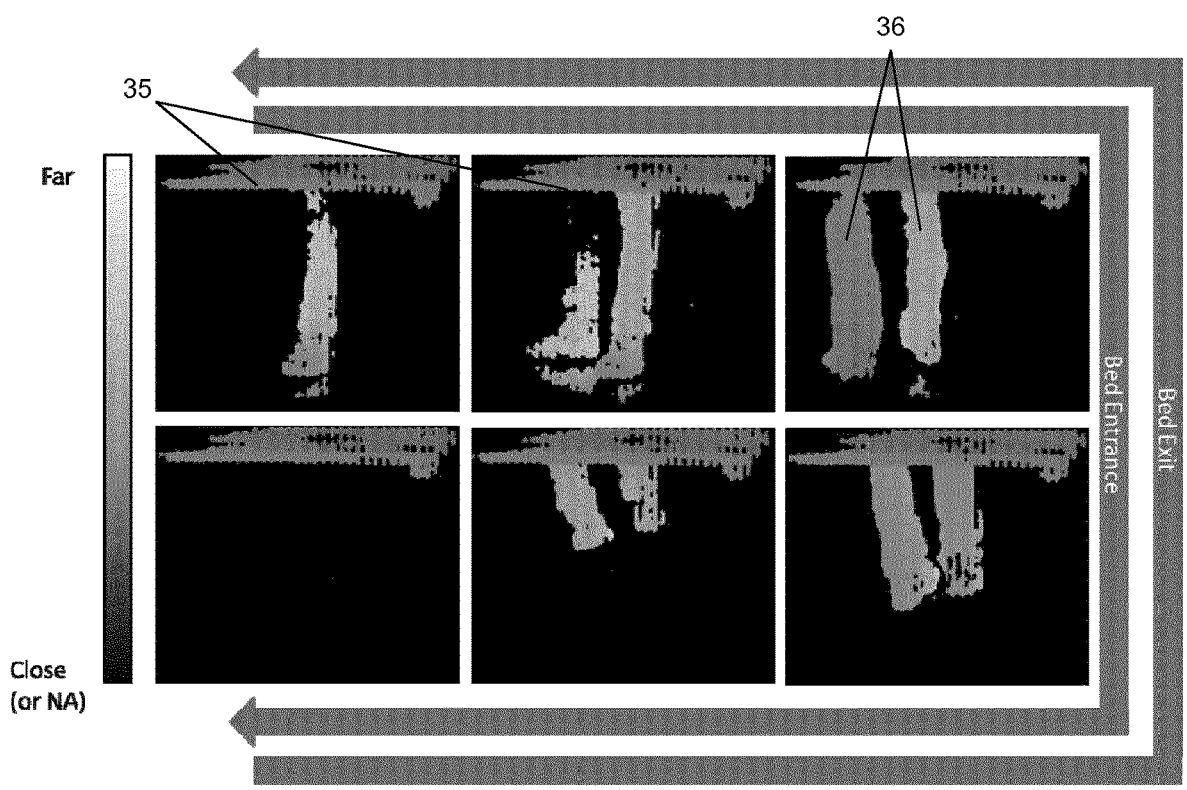
FIG. 3b shows an example series of depth images representing a subject exit event, according to an embodiment of the invention.

FIG. 3*b* shows an example set of images representing the same bed exit event (if followed anti-clockwise from the bottom left image), but obtained by a depth camera. It can be seen that the bed edge appears in the depth images as a well-defined edge feature 35, due to the relatively small and constant depth of the bed edge from the camera (as compared to the background). From the bottom middle image, the subject's legs appear as linear features 36 extending downwardly from the edge 35. The legs also appear as well-defined features during the time for which they are close to the bed. It can be seen that as the subject moves away from the bed (and therefore away from the camera), the definition of the leg features 36 decreases. However; it will be appreciated that segmentation of the leg features is a simpler task for the depth images of FIG. 3*b* than for the 2D images of FIG. 3*a*, since background objects are not visible at all in the depth images. Otherwise, detection and monitoring of features which appear contiguous with a detected edge can be performed in the same manner with depth images as with 2D images.

In some embodiments the time period over which the processing unit is arranged to monitor changes to a detected feature comprises a time period for which the feature is present in the received images. For example, in the scenario shown in FIGS. 3*a* and 3*b*, the time period begins with the bottom middle image, which is the earliest acquired image in which the leg features were present. In such embodiments the time period can end with an image which is the latest image in which the leg features were present. In such embodiments the processing unit 13 can determine a duration of the time period by comparing the acquisition time of the earliest acquired image in which the features were present to the acquisition time of the latest acquired image in which the features were present. In some embodiments the time period over which the processing unit is arranged to monitor changes to a detected feature comprises a time period having a fixed length, which begins with the earliest acquired image in which the detected feature is present.

In some embodiments the processing unit is arranged to generate a change signal based on a time series of values, e.g. feature property values, difference values, etc. The processing unit 13 can be arranged to use any suitable known signal analysis and feature extraction techniques in the detection and monitoring of features in the received images.

The processing unit 13 is further arranged to determine whether a change to a detected feature satisfies at least one predefined criterion for a subject exit event. In some embodiments the predefined criterion comprises a set of one or more conditions. In some embodiments the at least one predefined criterion for a subject exit event comprises a threshold (e.g. a minimum threshold) for a change to a given property of a detected feature over a time period. In some embodiments the at least one predefined criterion for a subject exit event comprises a condition specifying a direction of change (e.g. increase, decrease) of a detected feature over a time period. In some embodiments the at least one predefined criterion for a subject exit event comprises a condition relating to the direction of motion of a detected feature. In some embodiments the at least one predefined criterion for a subject exit event comprises a condition relating to the shape of a change signal. Conditions relating to the shape of a change signal can comprise any or all of: a measure of the variability of a change signal, an amount of time for which the variability of a change signal exceeds a predefined threshold, relative locations of peaks in a change signal, relative heights of peaks in a change signal, area under a change signal, frequency of periods when a change signal exceeds a predefined threshold, etc.

In some embodiments the predefined criterion for a subject exit event is defined such that motion of a detected feature in a direction away from the edge (i.e. the detected edge which the feature appeared contiguous with) during the time period will be determined by the processing unit to satisfy the predefined criterion and motion of a detected feature in a direction toward the edge will be determined by the processing unit not to satisfy the predefined criterion. In some such embodiments the processing unit 13 is arranged to determine that a direction of motion of a detected feature is away from the detected edge if a distance between a given part of the feature and the detected edge increases, on average, over a predefined time period (e.g. 1 minute) after the feature was first detected contiguous with the shadow.

In some embodiments the processing unit 13 comprises or is in communication with a memory storing a set of predefined change signatures corresponding to various different types of bed exit event (e.g. falling out of bed, sitting up and then getting out of bed, lowering the legs onto the floor from a prone position, etc.). A change signature may comprise, e.g., one or more change signals and/or sets of conditions relating to changes in one or more properties of a feature, of any of the types described above. In some such embodiments the at least one criterion comprises a change signature, and determining whether a change to a detected feature satisfies the at least one predefined criterion comprises determining whether a change signal generated for the detected feature matches the change signature. In some embodiments the processing unit 13 is further arranged to calculate confidence information in respect of each determination of whether the a change to a detected feature satisfies at least one predefined criterion for a subject exit event.

In some embodiments the predefined criterion for a subject exit event is defined such that changes to features representing persons or items other than the subject would not satisfy a predefined subject entry criterion For instance, a condition requiring a minimum rate of change can be included in the predefined criterion to exclude features corresponding to inanimate objects. In embodiments in which the camera is a depth camera, a condition requiring a feature to be closer than a minimum depth threshold can be included in the predefined criterion to exclude features corresponding to persons or objects in the vicinity of a monitored item of furniture but which are never located immediately adjacent an edge of the item of furniture. In some such embodiments a condition requiring a feature to be closer than the minimum depth threshold for a minimum amount of time can be included in the predefined criterion. In some embodiments the processing unit is provided with a set of predefined "other person" change signatures corresponding to various different movement patterns commonly exhibited by persons other than the subject (e.g. caregivers, cleaners, family members). In some such embodiments the predefined criterion for a subject exit event is defined such that a change signal generated for the detected feature which matches one of the "other person" change signatures is determined not to satisfy the predefined criterion.

The processing unit 13 is further arranged to output a signal based on the determining. In some embodiments the signal comprises a control signal, e.g. to a device having a wired or wireless communications link with the processing unit 13. Such a device could be, e.g., a communications device, a display device, an alarm device, etc. In such embodiments the control signal may be arranged, for example, to cause one or more of:

- an alarm device (e.g. a visual or audio alarm generating device) to generate an alarm;
- a communications device to generate a message to a caregiver;
- a communications device to generate a message to the subject;
- a communications device to send a signal to a remote device (e.g. a pager, PDA or mobile phone of a medical professional);
- a display device (e.g. a monitor or screen) to display information.

In some embodiments the signal comprises a message to a caregiver, e.g. indicating that a bed exit event has been detected. In some embodiments the signal comprises a message to the subject, e.g., to instruct them to remain in bed until assistance arrives. In some embodiments the processing unit is arranged to output a plurality of signals, for example a communications signal to a communications device such as a mobile phone of a medical professional, and a control signal to an alarm device causing it to generate an alarm.

In some embodiments in which the apparatus 10 comprises multiple cameras, each of the multiple cameras is for use underneath the same item of furniture. However, each of the multiple cameras is arranged to point in the direction of a different edge of the item of furniture, e.g. a first edge associated with a first side of the item of furniture and a second edge associated with a second, different side of the item of furniture. Each camera therefore captures images of a different background region adjacent the item of furniture. In some embodiments each camera views a background region adjacent a different side of the item of furniture from which it is possible for a subject to exit the item of furniture. Advantageously, embodiments which utilize multiple cameras to view regions adjacent different sides of the item of furniture enable every side of an item of furniture from which a subject could exit the item of furniture to be monitored, ensuring that an exit event is not missed by the apparatus 10. Such embodiments therefore have a high detection sensitivity.

Figure 4:
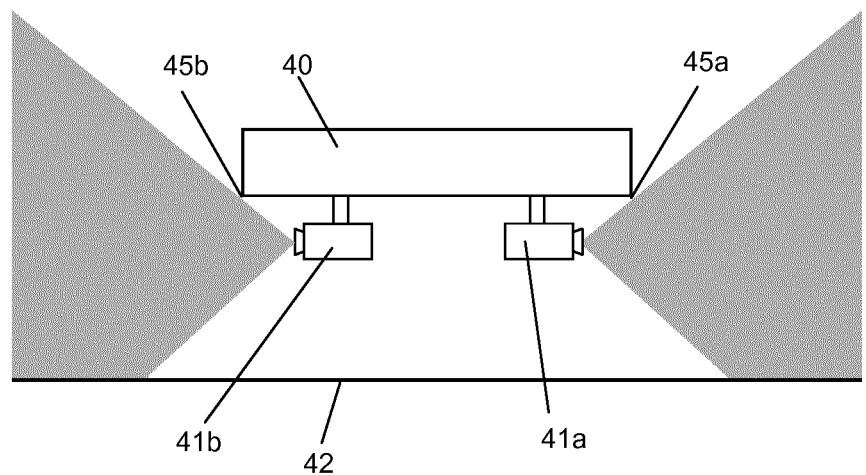
FIG. 4 shows an example apparatus comprising multiple cameras, according to an embodiment of the invention.

For example, FIG. 4 shows one such embodiment. In this embodiment a first camera 41a is fixed to a bed base of a bed 40 such that it views a background region adjacent a first side of the bed, and a second camera 41b is fixed to the bed base pointing in the opposite direction to the first camera, such that it views a background region adjacent a second side of the bed 40. The cameras 41a, 41b are arranged such that the edges 45a, 45b of the underside of the bed 40 are not included in the images captured by the cameras 41a, 41b. However, a processing unit of the apparatus in which the cameras 41a and 41b are comprised is arranged to detect a top edge of the images captured by the first camera 41a as a first edge which corresponds to the first side bed edge 45a, and to detect a top edge of the images captured by the second camera 41b as a second edge with corresponds to the second side bed edge 45b. In some such embodiments the processing unit 13 is arranged to detect the appearance of a feature contiguous with the first detected edge in the images captured by the first camera, and simultaneously to detect the appearance of a feature contiguous with the second detected edge in the images captured by the second camera. The motion of a detected feature is then analyzed by the processing unit 13 in the same manner, for both sets of images, and motion of one or more detected feature in each set of images may be simultaneously monitored.

In some embodiments the apparatus 10 is additionally for detecting when a subject has entered an item of furniture. In such embodiments the processing unit 13 is further arranged to determine whether a change to a detected feature over the time period satisfies at least one predefined criterion for a subject entry event. The at least one predefined criterion for a subject entry event may have any of the features described above in relation to the at least one criterion for a subject exit event. However, it will be appreciated that a subject entry event will typically involve changes (e.g. of feature properties) in the opposite direction to a subject exit event. For example, the property of feature area is expected to increase during a subject exit event (as shown by FIGS. 3a and 3b) and is expected to decrease during a subject entry event.

In some embodiments the predefined criterion for a subject entry event is defined such that motion of a detected feature over the time period in a direction away from the detected edge will be determined by the processing unit not to satisfy the predefined criterion. In some embodiments the predefined criterion for a subject entry event is defined such that changes to features representing persons or items other than the subject would not satisfy a predefined subject entry criterion (this can be achieved, e.g. in a similar manner to that discussed above in relation to the predefined criterion for a subject exit event). In some embodiments the processing unit 13 is further arranged to calculate confidence information in respect of each determination of whether a change to a detected feature satisfies at least one predefined criterion for a subject entry event. In embodiments for detecting subject entry events the processing unit 13 is further arranged to output a signal based on the determining of whether a change to a detected feature satisfies at least one predefined criterion for a subject entry event.

Figure 5:
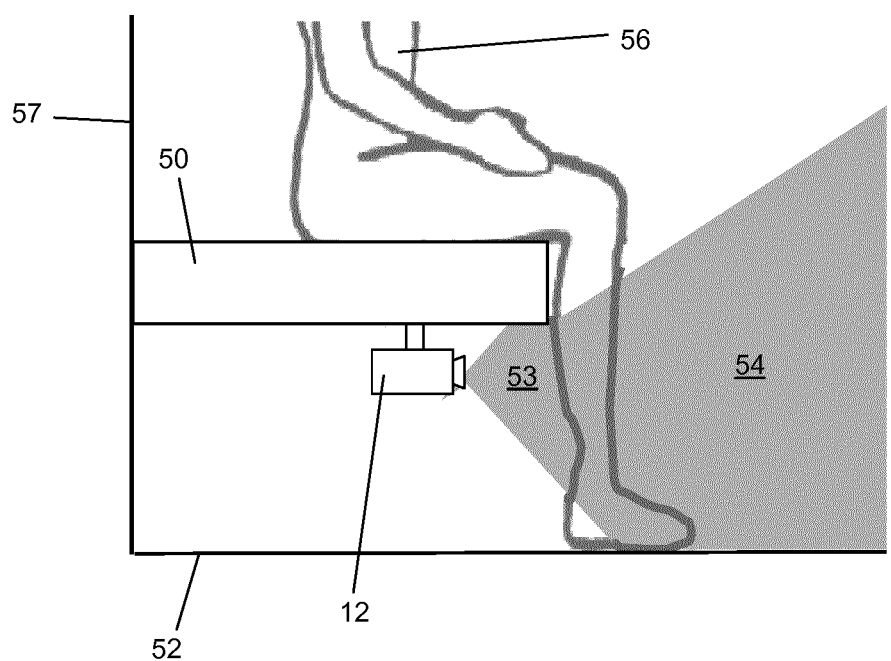
FIG. 5 shows a camera of the example apparatus of FIG. 1 in use during a subject exit event.

FIG. 5 shows the apparatus of FIG. 1 in use with an item of furniture 50, during a subject exit event. In this example the item of furniture comprises a hospital bed, which is positioned with one long side against a wall 57. However; in other examples the item of furniture can comprise another type of bed, a chair, a wheel chair, or any item of furniture which can be occupied by a subject.

A camera 12 is arranged below the hospital bed 50, such that an edge 55 of the underside of the bed 50 is included in images captured by the camera 12, as is foreground region 53 beneath the underside of the bed and a background region 54 adjacent the bed. The camera is preferably arranged such that the entire length of the side of the bed from which a subject may exit the bed 50 is within the FOV of the camera 12, such that a subject exiting the bed 50 must enter the FOV of the camera 12. In the example of FIG. 5, the camera 12 is attached to the base of the bed 50, e.g. by a mounting bracket. In other embodiments the camera is not attached to the item of furniture. Instead, the camera can be supported on the floor 52 underneath the item of furniture (e.g. by a stand or tripod). In the example of FIG. 5, a single camera is used because the bed 50 is arranged with one of the long sides against the wall 57, such that a subject 56 cannot exit the bed on that side. It will be appreciated, however, that if the bed 50 was positioned such that the subject 56 could exit from either long side, it would be desirable to provide two cameras, e.g. in the arrangement shown in FIG. 4.

When setting up the apparatus 10 with a particular item of furniture, decisions such as whether to attach the camera to the item of furniture, what angle to position the camera at with respect to the underside of the item of furniture, what height to position the camera at, etc., will be taken (e.g. by an engineer installing the apparatus 10) based on the exact configuration of the particular item of furniture. For example, many modern hospital beds are supported on complex mechanisms (e.g. for raising and lowering and/or changing the angle of the subject support surface) and when installing an apparatus 10 to monitor such a hospital bed, it will be necessary to ensure that the FOV of the camera is not obscured by any parts of the bed support mechanism. Preferably the camera (or multiple cameras) is positioned such that the FOV encompasses most or all of a side of the item of furniture from which a subject might exit that item of furniture.

When the subject 56 moves a part of their body over one of the long edges of the bed 50 and onto the floor 52 adjacent the bed, e.g. as part of a bed exit movement, that body part will enter the FOV of the camera 12, and will therefore appear in images captured by the camera 12. Consequently, when the subject is in the position shown in FIG. 5, the images acquired by the camera 12 will include two leg features extending downwardly from the bed edge 55. In images captured during the time period leading up to the situation shown in FIG. 5 (i.e. during the movement of the subject's legs towards the floor) the leg features will have appeared adjacent the bed edge 55 and will have increased in area and extension relative to the edge 55 over the time period. For example, the images captured by the camera 12 during this time period are expected to be similar to those shown by FIG. 3a (in embodiments in which the camera is a 2D camera) or FIG. 3b (in embodiments in which the camera is a depth camera). It will be appreciated that a bed entry event would appear, in the captured images, like a reversal of a bed exit event (i.e. one or more leg features detected contiguous with the shadow edge would shrink towards the bed edge 55 and would eventually disappear.

In some embodiments the camera 12 is manually activated, e.g. by person activating an on-switch of the camera, and captures images until manually deactivated, e.g. by a person activating an off-switch. In some embodiments the camera 12 is automatically activated, e.g. by a control signal from the processing unit 13. Preferably the camera 12 is only activated during times when the item of furniture is in use. For the purposes of the invention, an item of furniture is considered to remain "in use" during temporary absences of a subject using the item of furniture, e.g. to visit the bathroom, or to undergo treatment. By contrast, an item of furniture is considered to be not in use during the period between the discharge of a subject who was previously occupying that item of furniture, and the first occupation of that item of furniture by a new subject.

In use of the apparatus 10, the camera 12 is activated in one of the manners described above such that it continually captures sequential images having a foreground corresponding to a region 53 beneath the underside of the item of furniture 50 and a background corresponding to a region 54 adjacent the item of furniture 50. In some examples (such as the example of FIG. 5) the camera 12 captures images which include an edge of the item of furniture 50. In some embodiments the camera 12 continually captures images during the whole time the apparatus 10 is in use, such that the recording period comprises the period for which the apparatus 10 is in use. In some embodiments the camera 12 is activated in response to an event. In some such embodiments the event comprises a detection of motion of the subject 56 by a separate motion detector (e.g. an accelerometer attached to the item of furniture, or a separate camera-based motion detection system). In some embodiments the camera 12 is arranged to capture images for a predefined amount of time (i.e. the duration of the recording period is predefined). In some embodiments the captured images comprise video frames. In some embodiments the camera captures a series of still images.

Images captured by the camera 12 are sent to the processing unit 13. The processing unit 13 continually assesses, on the basis of the captured images, whether a subject exit event is occurring (or has occurred), e.g. by performing the method shown in FIG. 6. In some embodiments the processing unit 13 additionally continually assess, on the basis of the captured images, whether a subject entry event is occurring (or has occurred), e.g. by performing the method shown in FIG. 6.

Figure 6:
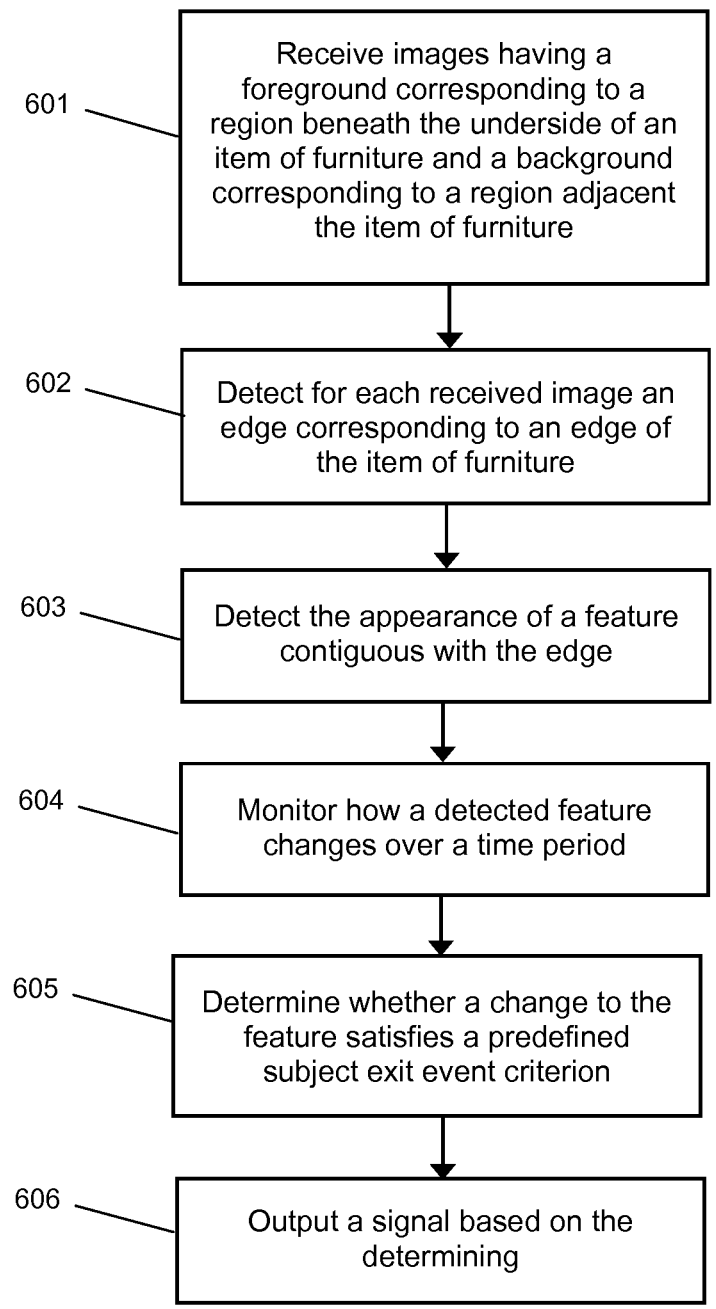
FIG. 6 is a flow chart illustrating a method for detecting when a subject has exited an item of furniture, according to a general embodiment of the invention.

FIG. 6 illustrates a method for detecting when a subject has exited an item of furniture. The item of furniture has an upper side for supporting a subject, and an underside opposite to the upper side. In a first step, 601, sequential images captured by a camera arranged below the underside of the item of furniture are received (e.g. by the processing unit 13). Each of the images does not include the upper side of the item of furniture and has a foreground corresponding to a region below the underside of an item of furniture and a background corresponding to a region adjacent the item of furniture. In some embodiments the images are received from the camera which captured the images, e.g. via a wired or wireless communication link. In some embodiments the images are received from a remote server (e.g. a central hospital server), e.g. via a wired or wireless communication link. In some embodiments the images are received on a machine-readable non-transitory storage medium. In some embodiments the images are received in real time or near-real time (i.e. as they are captured by a camera). In some embodiments the images are received from multiple sources, e.g. a first camera, arranged to monitor a first item of furniture, and a second camera, arranged to monitor a second item of furniture.

In step 602 an edge corresponding to an edge of the item of furniture is detected for each of the received images, e.g. by the processing unit 13. In some embodiments the edge corresponding to an edge of the item of furniture is detected in the manner described above in relation to the operation of the processing unit 13. In some embodiments performing step 602 comprises detecting the edge in each frame of a received video stream. In some embodiments performing step 602 comprises detecting the edge in each image of a received series of still images.

In step 603, the appearance of a feature contiguous with the edge is detected in the received images, e.g. by the processing unit 13. In some embodiments performing step 603 comprises detecting the appearance of a feature contiguous with the edge in the manner described above in relation to the operation of the processing unit 13. The result of step 603 may be a positive detection (i.e. it is detected that a feature has appeared contiguous with the edge) or a negative detection (i.e. it is detected that no features have appeared contiguous with the edge).

In step 604, how a feature which appeared contiguous with the edge changes over a time period is monitored, e.g. by the processing unit 13. In some embodiments performing step 604 comprises monitoring how a feature which appeared contiguous with the shadow edge changes over a time period in the manner described above in relation to the operation of the processing unit 13. In some embodiments step 604 is performed responsive to the result of step 603 being a positive detection. In some embodiments the monitoring of how a detected feature changes over a time period is updated each time a new image is received.

In step 605, it is determined (e.g. by the processing unit 13) whether a change to a feature which appeared contiguous with the shadow edge satisfies at least one criterion for a subject exit event. In some embodiments performing step 605 comprises determining whether a change to a feature which appeared contiguous with the edge satisfies least one predefined criterion for a subject exit event in the manner described above in relation to the operation of the processing unit 13. In some embodiments step 605 is performed continuously, e.g. each time the change monitoring is updated. In some embodiments the time period comprises a predefined time period, e.g. a time period starting with the detection of the appearance of the feature contiguous with the edge and having a predefined length. The determination generated by step 605 may be recalculated in respect of each newly-received image (or each subsequent frame of a video stream).

In step 606 a signal is output (e.g. by the processing unit 13) based on the determining (i.e. based on the result of step 605). In some embodiments performing step 606 comprises outputting a signal in the manner described above in relation to the operation of the processing unit 13. The signal may be output using a communications functionality of a monitoring device (e.g. the monitoring device 36). In some embodiments the signal is output continuously, in real-time or near-real time. In such embodiments, preferably the delay between the receipt of the images and the output of the signal is less than a few seconds, so that medical staff can react rapidly to a detected subject exit event. In some embodiments the signal contains a result of a determination of whether a detected change satisfies at least one predefined criterion for a subject exit event (e.g. an indication that a subject exit event is likely to be occurring/have occurred, if the criterion is satisfied, or an indication that a subject exit event is not likely to be occurring/have occurred, if the criterion is not satisfied). In some embodiments the signal contains confidence information associated with the result of the determination generated in step 605. In some embodiments step 606 is only performed if the result of step 605 is that the at least one criterion is met. In some embodiments the signal contains time information associated with the result of the determination, e.g. the time period during which the detected change(s) on which the determination was based occurred. In some embodiments the signal contains information about a movement type.

In preferred embodiments the method of FIG. 6 is performed continuously during a time period, e.g. a time period for which the apparatus 10 is operational. In some embodiments the method includes an additional step (not shown) of determining whether a change to a detected feature satisfies at least one predefined criterion for a subject entry event. In some embodiments performing this additional step comprises determining whether a change to a feature which appeared contiguous with the edge satisfies least one predefined criterion for a subject entry event in the manner described above in relation to the operation of the processing unit 13. In some embodiments this additional step is performed continuously, e.g. each time the change monitoring is updated. The determination generated by the additional step may be recalculated in respect of each newly-received image (or each subsequent frame of a video stream).

In some embodiments in which the method includes the additional step of determining whether a change to a detected feature satisfies at least one predefined criterion for a subject entry event, performing step 606 comprises outputting a signal based on the determining of whether a change to a feature satisfies at least one predefined criterion for a subject entry event. In some such embodiments performing step 606 comprises outputting a signal based on the determining of a change to a feature satisfies at least one predefined criterion for a subject entry event, and on a determining of whether a change to a feature satisfies at least one predefined criterion for a subject exit event.

Embodiments of the invention therefore advantageously enable exit of a subject from an item of furniture to be automatically detected, in an unobtrusive, reliable and computationally efficient manner.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. Apparatus for detecting when a subject has exited an item of furniture, the apparatus comprising:
   a camera adapted to be arranged, when in use, beneath the underside of an item of furniture, wherein the item of furniture has an upper side for supporting a subject and the underside is opposite to the upper side, and wherein the camera is arranged to capture sequential images that do not include the upper side of the item of furniture, the images having a foreground corresponding to a region beneath the underside of the item of furniture and a background corresponding to a region adjacent the item of furniture; and
   a processing unit arranged to:
      receive the images from the camera;
      detect, for each received image, an edge corresponding to an edge of the item of furniture;
      detect, in the received images, the appearance of a feature contiguous with the edge;
      monitor how the detected feature changes over a time period;
      determine whether a change to the detected feature over the time period satisfies at least one predefined criterion for a subject exit event; and
      output a signal based on the determining.

2. The apparatus of claim 1, wherein the camera is arranged to capture sequential images including at least part of the underside of the item of furniture, wherein the edge corresponding to an edge of the item of furniture comprises an edge of the at least part of the underside of the item of furniture, such that a first portion of each image adjacent a first side of the edge shows the underside of the item of furniture and a second portion of each image adjacent a second, opposite side of the edge does not show the underside of the item of furniture.

3. The apparatus of claim 1, wherein the processing unit is arranged to detect a predefined one of the edges of each received image to be an edge corresponding to an edge of the item of furniture.

4. The apparatus of claim 1, wherein the processing unit is arranged to detect the appearance of a feature contiguous with the edge by:
   comparing a first image acquired at a first time, to a second image acquired at a second, later, time; and
   if a feature contiguous with the edge is present in the second image but is not present in the first image, determining the detected feature that is contiguous with the edge as the feature contiguous with the edge that is present in the second image but that is not present in the first image.

5. The apparatus of claim 1, wherein the camera comprises a depth camera and the criterion for a subject exit event includes a condition requiring the detected feature to be closer than a minimum depth threshold.

6. The apparatus of claim 1, wherein the camera comprises a wide-angle camera.

7. The apparatus of claim 1, wherein the camera is arranged beneath the underside of the item of furniture.

8. The apparatus of claim 1, wherein the processing unit is arranged to monitor changes to the detected feature over a time period by:
   determining a first value for a property of the detected feature in a first image acquired at a first time;
   determining a second value for the property of the detected feature in a second image acquired at a second, later, time; and
   comparing the second value to the first value.

9. The apparatus of claim 8, wherein the property of the detected feature is any one of: size of the feature, shape of the feature, location of the feature; extension of the feature perpendicular to the shadow edge; depth of the feature.

10. The apparatus of claim 8, wherein the processing unit is arranged to monitor changes to the detected feature over a time period by:
    determining a rate of change of the detected feature over the time period, based on the first value, the second value, the acquisition time of the first image, and the acquisition time of the second image.

11. The apparatus of claim 8, wherein the processing unit is arranged to monitor changes to the detected feature over a time period by determining a direction of motion of the detected feature over the time period; and wherein the at least one predefined criterion for a subject exit event comprises a condition relating to a direction of motion of the detected feature.

12. The apparatus of claim 11, wherein the predefined criterion for a subject exit event is defined such that motion of the detected feature in a direction away from the edge during the time period will be determined by the processing unit to satisfy the predefined criterion and motion of the detected feature toward the edge will be determined by the processing unit not to satisfy the predefined criterion.

13. The apparatus of claim 11, wherein the predefined criterion for a subject exit event is defined such that motion of the detected feature in a direction into the plane of the received images during the time period will be determined by the processing unit to satisfy the predefined criterion and motion of the detected feature out of the plane of the received images will be determined by the processing unit not to satisfy the predefined criterion.

14. The apparatus of claim 11, wherein the apparatus is additionally for detecting when a subject has entered an item of furniture and the processing unit is further arranged to determine whether a change to the detected feature over the time period satisfies at least one predefined criterion for a subject entry event; and wherein the predefined criterion for a subject entry event is defined such that motion of the detected feature over the time period in a direction away from the shadow edge or into the plane of the received images will be determined by the processing unit not to satisfy the predefined criterion.

15. A system for detecting when a subject has exited an item of furniture, the system comprising:
    an item of furniture having an upper side for supporting a subject and an underside opposite to the upper side;
    a camera adapted to be arranged, when in use, beneath the underside of the item of furniture, arranged to capture sequential images that do not include the upper side of the item of furniture, the images having a foreground corresponding to a region beneath the underside of the item of furniture and a background corresponding to a region adjacent the item of furniture; and a processing unit arranged to:
receive the images from the camera;
detect, for each received image, an edge corresponding to an edge of the item of furniture;
detect, in the received images, the appearance of a feature contiguous with the edge;
monitor how the detected feature changes over a time period;
determine whether a change to the detected feature over the time period satisfies at least one predefined criterion for a subject exit event; and
output a signal based on the determining.

16. The system of claim 15, wherein the processing unit is arranged to detect the appearance of a feature contiguous with the edge by:
comparing a first image acquired at a first time, to a second image acquired at a second, later, time; and
if a feature contiguous with the edge is present in the second image but is not present in the first image, determining that a feature has appeared contiguous with the edge.

17. The system of claim 15, wherein the processing unit is arranged to monitor changes to a detected feature over a time period by:
determining a first value for a property of the feature in a first image acquired at a first time;
determining a second value for the property of the feature in a second image acquired at a second, later, time; and
comparing the second value to the first value.

18. A method for detecting when a subject has exited an item of furniture, wherein the item of furniture has an upper side for supporting a subject, and the underside is opposite to the upper side, the method comprising:
receiving sequential images captured by a camera arranged beneath the underside of the item of furniture, the images not including the upper side of the item of furniture and having a foreground corresponding to a region beneath the underside of an item of furniture and a background corresponding to a region adjacent the item of furniture;
detecting, for each received image, an edge corresponding to an edge of the item of furniture;
detecting, in the received images, the appearance of a feature contiguous with the edge;
monitoring how the detected feature changes over a time period;
determining whether a change to the detected feature over the time period satisfies at least one predefined criterion for a subject exit event; and
outputting a signal based on the determining.

19. The method of claim 18, wherein the detecting of the appearance of a feature contiguous with the edge includes:
comparing a first image acquired at a first time, to a second image acquired at a second, later, time; and
if a feature contiguous with the edge is present in the second image but is not present in the first image, determining that a feature has appeared contiguous with the edge.

20. The method of claim 18, wherein the monitoring of changes to a detected feature over a time period includes:
determining a first value for a property of the feature in a first image acquired at a first time;
determining a second value for the property of the feature in a second image acquired at a second, later, time; and
comparing the second value to the first value.

* * * * *